Figure 1:
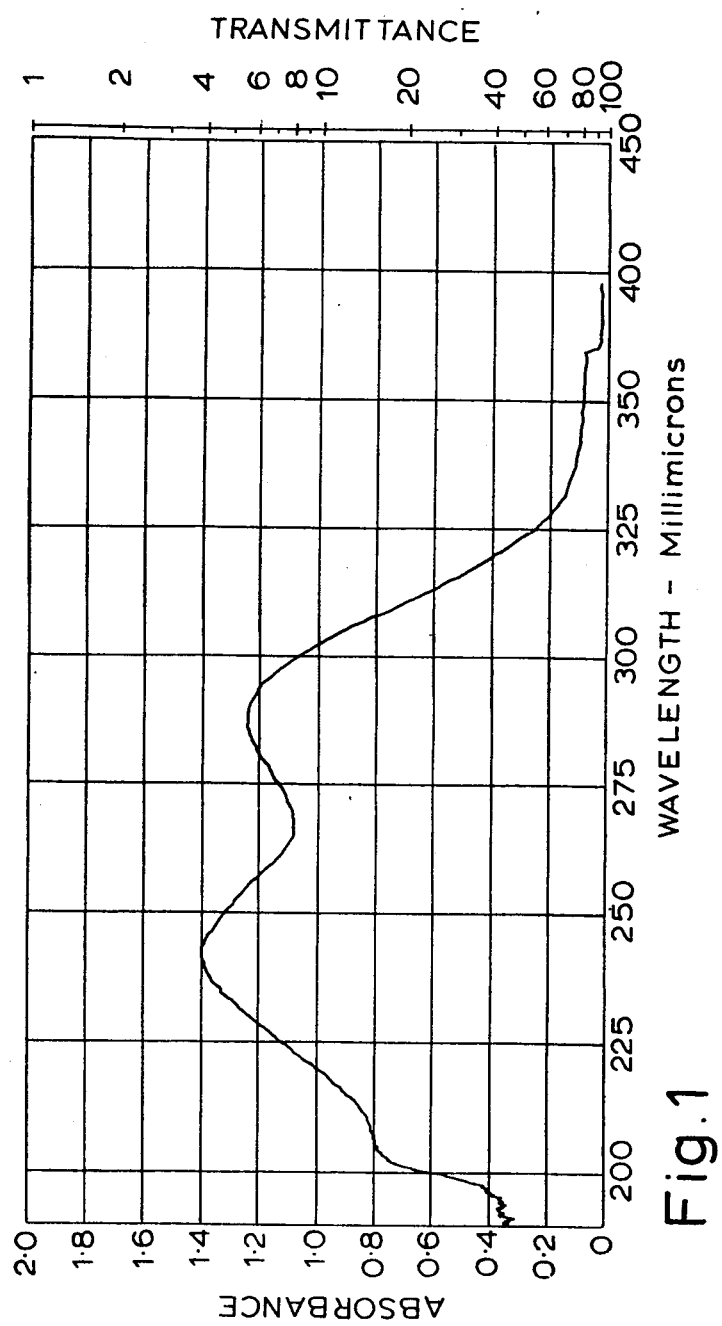

United States Patent [19]

Cole et al.

[11] 4,203,973

[45] May 20, 1980

[54] ANTIBIOTICS

[75] Inventors: Martin Cole, Dorking; John D. Hood, Cranleigh; Dennis Butterworth, Redhill, all of England

[73] Assignee: Beecham Group Limited, England

[21] Appl. No.: 913,304

[22] Filed: Jun. 7, 1978

Related U.S. Application Data

[60] Division of Ser. No. 724,948, Sep. 20, 1976, which is a continuation-in-part of Ser. No. 691,491, Jun. 1, 1976, abandoned, which is a division of Ser. No. 559,973, Mar. 19, 1975, abandoned.

[30] Foreign Application Priority Data

Mar. 28, 1974 [GB] United Kingdom ............... 13855/74

[51] Int. Cl.$^2$ ............................................ A61K 35/00
[52] U.S. Cl. .................................................... 424/114
[58] Field of Search ......................................... 424/114

Primary Examiner—Jerome D. Goldberg
Attorney, Agent, or Firm—Jacobs & Jacobs

[57] ABSTRACT

It has been found that an antibiotic can be obtained by the fermentation of certain strains of *Streptomyces olivaceus* and related organisms and when pure this antibiotic is an extremely potent inhibitor of many $\beta$-lactamases. This antibiotic which we designate MM 4550A may be obtained in substantially pure form by the chromatographic purification of the crude antibacterial complex obtained from the culture medium.

26 Claims, 3 Drawing Figures

ANTIBIOTICS

CROSS-REFERENCE

This is a division of Ser. No. 724,948 filed Sept. 20, 1976 which is a CIP of 691,491, filed June 1, 1976 which is divisional of Ser. No. 559,973 filed March 19, 1975, both abandoned.

BACKGROUND OF THE INVENTION

British Pat. No. 1,363,075 disclosed that a useful β-lactamase inhibitor could be obtained by the fermentation of certain strains of *Streptomyces olivaceus*. Until our present invention, it was believed that the material disclosed in British Pat. No. 1,363,075 was substantially pure. However, we have discovered that this is not so and that a very minor component of that material can be isolated and has extremely potent β-lactamase inhibitory activity. This new material is designated MM 4550A and it is believed to be responsible for a major part of any β-lactamase inhibitory activity present in the material of British Pat. No. 1,363,075 although it is responsible for only a very minor part of the antibacterial activity which may be exhibited by that material. Naturally, nothing in this specification should be construed as claiming material as disclosed in British Pat. No. 1,363,075. Other β-lactamase inhibitors are known to be produced by strains of *Streptomyces olivaceus*, for example those disclosed in German Published Patent Application No. 2,340,005, but such materials do not have the potent β-lactamase inhibitory activity of substantially pure MM 4550A. United States Pat. No. 3,950,357 disclosed that *Streptomyces cattleya* produced the antibiotic Thienamycin which has the structure:

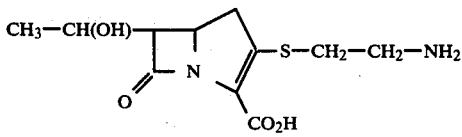

Based on the present knowledge of the structure of MM 4550A, significant structural differences are apparent between thienamycin and MM 4550A.

DESCRIPTION OF THE INVENTION

The present invention provides substantially pure MM 4550A and its salts.

MM 4550A is a solid carboxylic acid which in the form of a substantially pure sodium salt has the following characteristics:

i. It is highly soluble in water, soluble in methanol and substantially insoluble in chloroform, diethylether and hydrocarbons.

ii. In aqueous solution, it has a characteristic ultraviolet spectrum with absorption maxima at about 238 nm. and at about 287 nm.

iii. When present at 0.4% w/w in a freshly prepared KBr disc, it has a characteristic infra-red spectrum which has absorption maxima at, inter alia, about 3450, 2950, 1765, 1695, 1510, 1390 and 1260 cm$^{-1}$. If a further spectrum is taken about one week after the preparation of the KBr disc, the spectrum shows considerable changes, for example, the large peak previously at about 1765 cm$^1$ is considerably reduced in size or is absent.

iv. It has a characteristic n.m.r. spectrum when taken in D$_2$O which spectrum possesses, inter alia, (a) a pair of low field doublets centered approximately at 2.45τ and 3.65τ with coupling constants of approximately 15 Hz; (b) a doublet centered at approximately 8.55τ and (c) a sharp singlet at approximately 7.95τ.

v. It possesses antibacterial activity against various species including, inter alia, strains of *Staphylococcus aureus, Bacillus subtilis, Escherichia coli, Klebsiella aerogenes, Proteus mirabilis, Acinetobacter anitratus, Serratia marcescens* and *Shigella sonnei*.

vi. When mixed with ampicillin, it synergizes its activity against organisms including strains of *Escherichia coli, Klebsiella aerogenes, Proteus mirabilis, Proteus morganii* and *Staphylococcus aureus Russell*.

vii. Amino acid analysis indicates that the material is not a polypeptide or protein. No α-aminoadipic acid is found after acid hydrolysis.

viii. It reacts with Ehrlich's reagent (300 mg. of 4-dimethyl-aminobenzaldehyde dissolved in a mixture of 54 ml. n-butanol, 9 ml. ethanol and 9 ml. concentrated hydrochloric acid) to produce a blue color on paper chromatograms and tlc sheets.

ix. It is not a general enzyme poison and does not inhibit the following enzymes at concentrations in excess of those required to inhibit the β-lactamase of *Escherichi coli*; monoamine oxidase, carbonic anhydrase, dopa decarboxylase, trypsin, chymotrypsin or urease. When run over cellulose in a thin layer chromatography system di-sodium MM 4550A has the following approximate R$_f$ values:

(a) Butanol/isopropanol/water—7:7:6; R$_f$=0.7
(b) isopropanol/water—7:3; R$_f$=0.6
(c) n-butanol/ethanol/water—7:7:6; R$_f$=0.7
(d) n-propanol/water—4:1; R$_f$=0.6

When run over silica gel (Merck F.254) in a thin layer chromatography system di-sodium MM 4550A has the following approximate R$_f$ values:

(e) n-propanol/phosphate buffer 0.1 M pH7—7:3; R$_f$=0.6
(f) n-butanol/methanol/water—4:1:2; R$_f$=0.34

When substantially pure the di-sodium salt of MM 4550A has an I$_{50}$ (as hereinafter described) of less than 0.0001 μg/ml against the β-lactamse of *Escherichia coli* B 11.

From another viewpoint MM 4550A may be characterized as a sulphur-containing β-lactamase inhibitory compound produced by *Streptomyces olivaceus* ATCC 31126 for which an aqueous solution of the di-sodium salt has UV absorption maxima at about 238 nm and at about 287 nm. This spectrum may be seen from FIG. 1.

Figure 2:
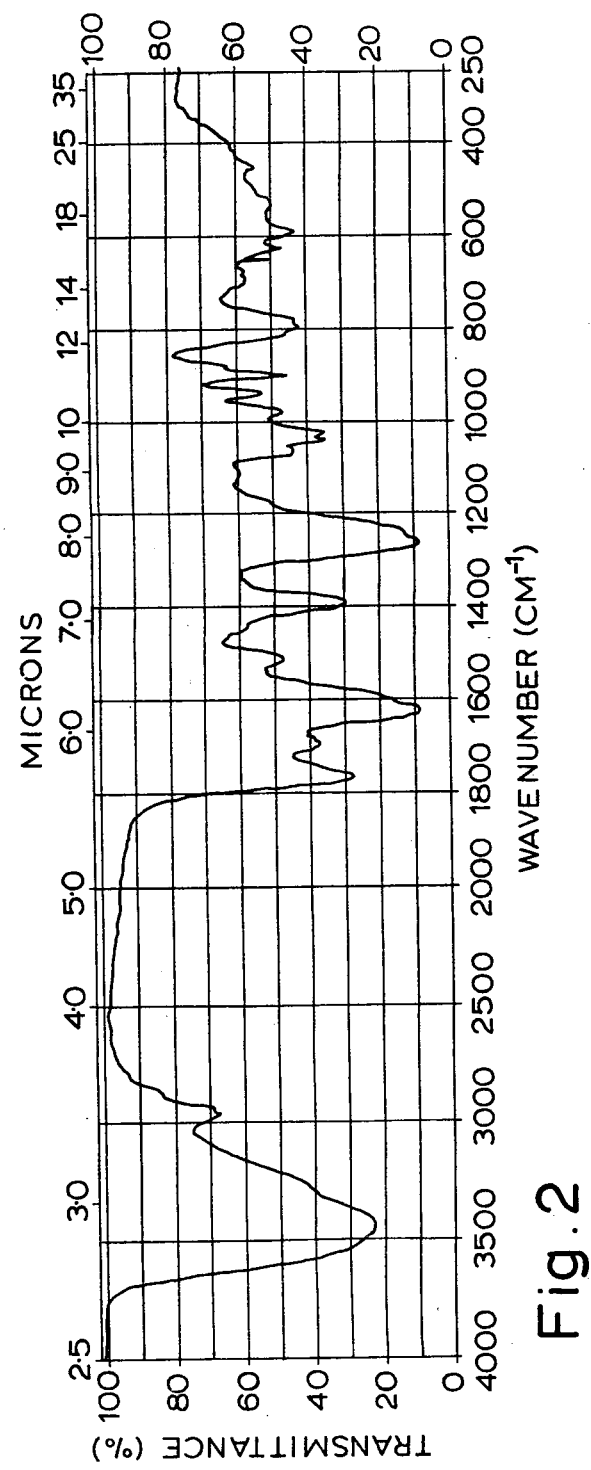
Figure 3:
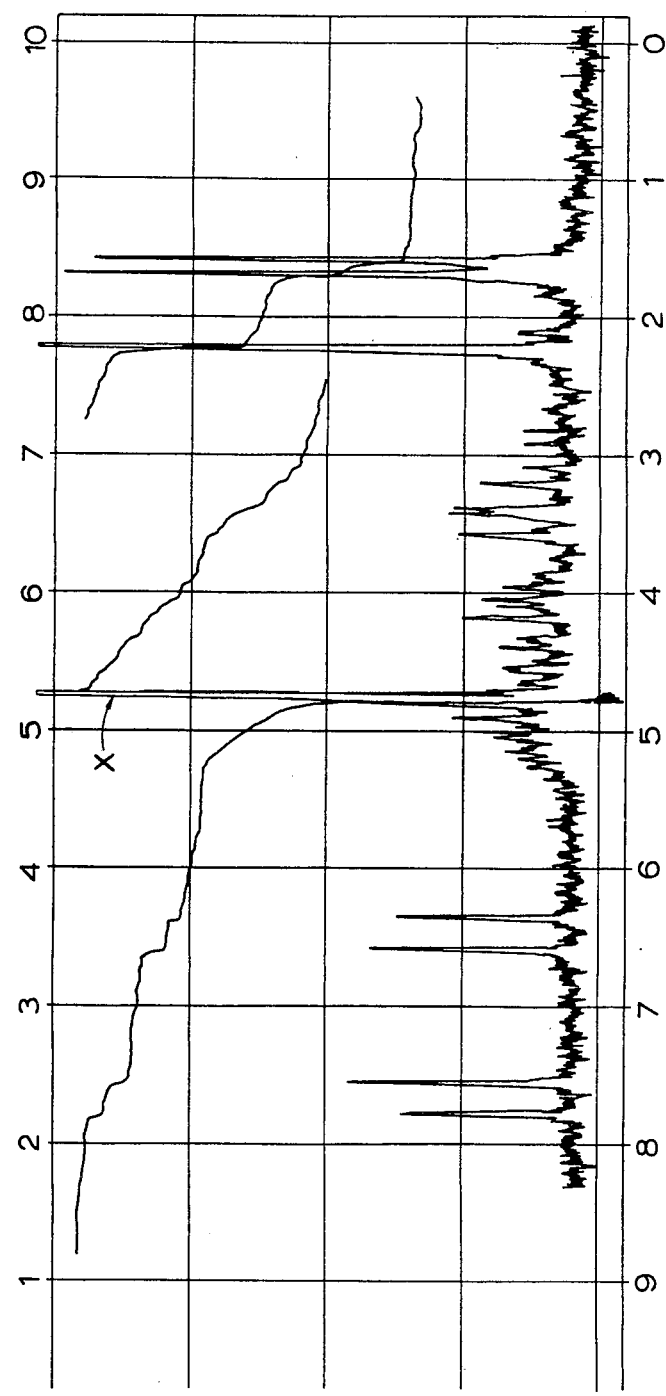

Alternatively, MM 4550A may be characterized as an antibacterial agent which in the form of its substantially pure di-sodium salt has an infra-red absorption spectrum substantially as shown in FIG. 2. when taken in a freshly prepared 0.4% w/w KBr disc and has an n.m.r spectrum substantially as shown in FIG. 3 when taken in a freshly prepared solution in D$_2$O.

MM 4550A has the molecular formula C$_{13}$H$_{16}$O$_9$N$_2$S$_2$.

MM 4550A is believed to have the structural formula:

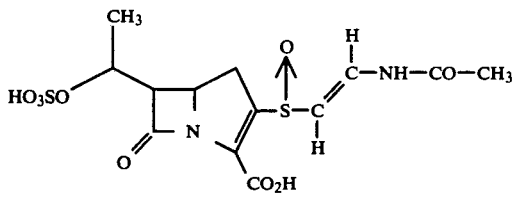

MM 4550A tends to be unstable when in the unsalted acid form. Accordingly, a preferred aspect of this invention provides salts of MM 4550A. Most suitably these salts are those formed with pharmaceutically acceptable ions such as sodium, potassium, calcium, magnesium, aluminium, conventional substituted ammonium ions and the like. Particularly suitable salts are alkali metal salts such as the sodium or potassium salts, for example, the di-sodium or di-potassium salts.

Suitably MM 4550A and its salts as provided by this invention are at least 50% pure, more suitably at least 70% pure and preferably 80% pure, for example 90–100% pure. In a further aspect this provides a pharmaceutical composition which comprises MM 4550A as hereinbefore described or a salt thereof together with a pharmaceutically acceptable carrier.

Most suitably the compositions of this invention contain a sodium or potassium salt of MM 4550A, for example, the di-sodium or di-potassium salt of MM 4550A.

Such compositions may be in a form suitable for oral, topical or parenteral use. For example, tablets, capsules, creams, syrups, reconstitutable powders and sterile forms suitable for injection or infusion may be used. Such compositions may contain conventional pharmaceutically acceptable materials such as diluents, binders, colours, flavours, preservatives, disintegrants and the like in accordance with conventional pharmaceutical practice in a manner well known to those skilled in the formulation of antibiotics such as penicillins and cephalosporins.

The MM 4550A or its salts may be present in the composition of the invention as sole therapeutic agent or it may be present together with a β-lactam antibiotic. Suitable β-lactam antibiotics include those known to be susceptible to β-lactamases and also having some intrinsic resistance to β-lactamases. Such β-lactam antibiotics include ampicillin, amoxycillin, benzylpenicillin, phenoxymethylpenicillin, propicillin, cephaloridine, cefoxitin, cephalothin, cephalexin, carbenicillin, ticarcillin and in vivo hydrolysable esters of such compounds such as the phenyl, tolyl or indanyl esters of carbenicillin or ticarcillin or the acetoxymethyl, pivaloyloxymethyl or phthalidyl esters of ampicillin, benzylpenicillin, amoxycillin, cephaloridine, cephaloglycin and the like.

The ratio of MM 4550A or salt thereof to β-lactam antibiotic is normally between 10:1 and 1:10, for example, between 3:1 and 1:3.

The total quantity of antibacterial agents present in any unit dosage form will normally be between 50 and 1500 mgs and will usually be between 100 and 1000 mgs.

Preferred unit dosage compositions according to this invention may be administered one or more times a day, for example, 2 to 4 times a day, in the treatment of diseases of the urinary tract, respiratory tract, soft tissues and the like. Thus the compositions may be used in the treatment of such diseases as bronchitis, gonorrhea, otitus media, mastitis and the like.

In one of its aspects, this invention provides a process for the preparation of MM 4550A or a salt thereof which comprises chromatographically separating a solution of MM 4550 (Complex) as hereinafter described into fractions consisting essentially of a solution of MM 4550A or a salt thereof and other fractions and isolating the MM 4550A or a salt thereof from solution.

By those fractions "consisting essentially of a solution of MM 4550A or a salt thereof" is meant that either the only antibiotic material present in that solution is MM 4550A or a salt thereof or that if any other antibiotic material is present then it is there to a lesser extent than the MM 4550A or salt thereof. More suitably MM 4550A or a salt thereof represents 70%, most suitably 80% and preferably 90–100%, of the antibiotic material present in the fraction. We have found that an acceptable method of determining which fractions consist essentially of a solution of MM 4550A or a salt thereof is to moniter the uv absorption spectrum of each sample. Those fractions showing a uv spectrum similar to that of FIG. 1 normally contain MM 4550A or a salt thereof substantially free from other antibiotic material such as MM 13902 as hereinafter described. In general those fractions showing a distinct uv absorption maximum at about 285 nm are of the desired purity.

Normally the preceeding process is used for the isolation of MM 4550A as a dibasic salt. If a monobasic salt of MM 4550A or the free acid MM 4550A per se is required, they may be prepared by the acidification of a dibasic salt of MM 4550A because in general the monobasic salts of MM 4550A and the free acid MM 4550A are not sufficiently stable to isolate from mixtures such as MM 4550 (Complex) as hereinafter described. These monobasic salts and free acid are not readily obtainable owing to their low stability.

As previously stated, we believe that the chromatographic isolation of MM 4550A is best carried out using a salt of MM 4550A such as the di-sodium salt. Salts of MM 4550A are more soluble in aqueous solvent systems than in highly lipophilic solvents and consequently it is preferred to use aqueous solvent systems in the chromatographic purifications used in this invention.

In our hands aqueous solutions of electrolytes buffered to approximately neutrality have proved suitable for use in conjunction with polar support materials such as basic ion-exchange resins. Thus an aqueous solution of sodium chloride buffered to about pH 7 with a conventional buffer such as a phosphate buffer may be used in conjunction with support materials which may contain tertiary amino groups or quaternary ammonium groups. We have found that basic ion-exchange celluloses and basic ion-exchange cross linked dextrans are suitable support materials and that QAE Sephadex A25 in particular is a highly suitable support material especially when the solvent system comprises 0.7 m sodium chloride in pH 7 phosphate buffer. ('Sephadex' is a Registered Trade Mark).

Alternatively, in our hands solvent systems comprising mixtures of water and water viscible organic solvent such as a lower alkanol have proved suitable for use in conjunction with inert support materials such as silica gel or cellulose. A particularly suitable solvent system for use with cellulose is a mixture of water and isopropanol, especially a 7:3-isopropanol:water mixture.

However, the product of the above procedures frequently contains a very high proportion of sodium chloride so that it is beneficial to de-salt the pooled solutions. De-salting may be effected by passing the solution down a column containing a lipophilic material onto which the MM 4550A is adsorbed but which does not adsorb the sodium chloride. Suitable column materials include polystyrenes such as Amberlite XAD 4 and gel filtration agents such as cross linked dextrons such as Sephadex G 25 and polyacrylamide gels such as Biogel P2 ('Amberlite', 'Sephadex' and 'Biogel' are Trade Marks). The antibiotic may be eluted from the column using water, aqueous methanol or the like.

When the desired solutions are obtained by the above process the di-basic salt of MM 4550A may be obtained in solid form by the removal of the solvent under mild conditions. We have found that an acceptable method of obtaining such solid material is to freeze-dry the pooled fractions containing MM 4550A.

If desired the preceeding process may be carried out in two or more steps. For example, a solution of MM 4550 (Complex) may be separated into fractions comprising MM 4550A or salt thereof contaminated with up to its own weight of other antibacterial agents, the fractions may be freeze dried to yield a material containing, for example, about 50-60% of MM 4550A or a salt thereof and this material may then be rechromatographed to yield a material which contains, for example, 90-100% of MM 4550A or a salt thereof.

For the purpose of this specification the term "MM 4550 (Complex)" is used to describe the material originally designated as MM 4550 in British Pat. No. 1,363,075. MM 4550 (Complex) as produced on repetition of the Examples of British Pat. No. 1,363,075 is an impure material which contains in various proportions salts of MM 13902 (as described hereinafter) and salts of MM 4550A and considerable quantities of other materials. MM 4550 (Complex) does not have the characteristic ultra-violet spectrum of MM 4550. The $I_{50}$ (as described hereinafter) of MM 4550 (Complex) produced by repetition of the Examples of British Pat. No. 1,363,075 is not normally below 0.0004 ug/ml. The ratio of salts of MM 4550 and salts of MM 13902 present in MM 4550 (Complex) is believed to be highly variable and is thought to depend on such factors as the strain of organism used and/or the exact isolation techniques used but it has been generally found that the complex contains more MM 4550A than MM 13902. The preparation of MM 4550 (Complex) is described hereinafter in the section relating to "Descriptions".

For the purpose of this specification the term "MM 13902" is used to describe a substantially pure compound which is a potent antibacterial agent and which also possesses a certain degree of β-lactamase inhibitory activity. The properties of MM 13902 are described hereinafter in the section relating to "Descriptions".

In an alternative view, this invention provides a process for the preparation of MM 4550A and its salts which process comprises the cultivation of a MM 4550A producing strain of Streptomyces and thereafter recovering the MM 4550A or salt thereof from the culture.

For this process we have found that MM 4550A producing strains are strains of *Streptomyces olivaceus* and related organisms as described hereinafter.

Most suitably the organism used is a strain of *Streptomyces olivaceus* such as ATCC 21379, 21380, 21381, 21382, 31126 or mutants thereof.

A particularly preferred organism for use in this process is *Streptomyces olivaceus* ATCC 31126.

When used herein, the term "cultivation" means the deliberate aerobic growth of an organism in the presence of assimilable sources of carbon, nitrogen, sulphur and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined. In our hands we have found media containing complex nutrients such as yeast extract, soya bean flour and the like to be particularly suitable. We have also found that the addition of cobalt ions, sulphate ions and calcium carbonate to be beneficial.

We have found that cultivation at a temperature of 28°±2° C. gives acceptable yields of antibiotic and that a good time to harvest the broth is 2-3 days after the initiation of fermentation.

When used herein the term "mutant" includes any mutant strain which arises spontaneously or through the effect of an external agent whether that agent is applied deliberately or otherwise. Suitable methods of producing mutant strains include those outlined by H. I. Adler in Techniques for the Development of Micro-organisms in "Radiation and Radioisotopes for Industrial Micro-organisms", Proceedings of a Symposium, Vienna, 1973, page 241, International Atomic Energy Authority and these include:

i. Ionising radiation (such as X- and Y- rays), uv light, uv light plus a photosensitizing agent (such as 8-methoxypsoralen), nitrous acid, hydroxylamine, pyrimidine base analogues (such as 5-bromouracil), acridines, alkylating agents (such as mustard gas, ethyl-methane sulphonate), hydrogen peroxide, phenols, formaldehyde, heat, and ii. Genetic techniques such as recombination, transformation, transduction, lysogenisation, lysogenic conversion and selective techniques for spontaneous mutants.

We have found that use of a mutation promoting agent can lead to the production of organisms which have the ability to produce enhanced quantities of the desired antibiotics. For example, irradiation of cultures of *Streptomyces olivaceus* ATCC 21379 followed by isolation of the resulting strain which appeared to produce the largest zone of activity on the KAG assay as hereinafter described lead to the isolation of *Streptomyces olivaceus* ATCC 31126 which is a preferred strain for use in this invention.

In general, all isolation and purification procedures used in obtaining the desired antibiotic should take place at non-elevated temperatures, for example, below 20° C. and more suitably not above 12° C.

The desired product is normally obtained predominantly from the culture filtrate so that the preferred initial step in the isolation process is the removal of solid material from the fermentation, for example by filtration.

An impure preparation of MM4550A or a salt thereof may be obtained from the clarified culture filtrate by adsorbing the MM 4550A or a salt thereof onto an active material such as active carbon or the like and thereafter eluting the desired substance from the active material using a solvent such as aqueous acetone. Normally this process is carried out on a di-basic salt of MM 4550A.

Alternatively an impure preparation of MM 4550A or a salt thereof may be obtained from the culture filtrate by extraction using a lipophilic ammonium salt and a water immiscible solvent. This is frequently more effective than the process preceding adsorption described above. (The MM 4500A may be obtained as the substituted ammonium salt by evaporation of the organic solvent under reduced pressure.) Preferably the initial solution of the MM 4550A substituted ammonium salt is then back extracted into an aqueous phase by using a solution of an alkali metal iodide such as sodium iodide. This last process variant generally leads to preparation of an aqueous solution of an impure di-basic salt of MM 4550A.

The impure forms of MM 4550A or its salts as described above are normally subjected to the chromatographic procedures hereinbefore described in order to produce material of acceptable purity.

The following Descriptions elucidate general information useful in the isolation of antibacterial compounds. The following Examples are illustrative of aspects of the invention.

DESCRIPTION 1

$I_{50}$ Determination

The $I_{50}$ value is the amount of material required to give 50% inhibition of hydrolysis of ampicillin by the $\beta$-lactamase enzyme of *Escherichia coli* B11, an organism containing an R factor controlled $\beta$-lactamase. This $\beta$-lactamase is classified as a type IIIa enzyme according to the classification of Richmond and Sykes [Adv. in Microbiol.Physiol. 9 31 (1973)]

The rate of $\beta$-lactamase hydrolysis of ampicillin to its penicilloic acid can be followed by a starch-iodometric assay in which one measures the rate of formation of penicilloic acid by following the decolorization of a starch-iodine complex. This method and the preparation of the $\beta$-lactamase are described in a paper by Cole M., Mlson S., and Fullbrook P.D. (Biochemical Journal 1972, 127, 295–308). A slight modification of the above method was used in that the sample of inhibitor was preincubated with the enzyme for 15 minutes at 37° C. prior to adding the substrate ampicillin. The procedure was as follows:

| Reagents | |
| --- | --- |
| Buffer: | 0.05M pH7 potassium phosphate buffer |
| Starch/iodine solution: | Prepared as described by Novick, Biochemical J. (1962) 83, 236 |
| Substrate: | Ampicillin 40 $\mu$g/ml in buffer |
| $\beta$-lactamase Enzyme: | Prepared from *E.coli* B11 as described by Cole et al, Biochem. J.(1972) 127, 295. The dilution of the enzyme preparation in buffer was such as to give a fall of about 0.3 optical density units per 100 secs. in the uninhibited reaction. Other $\beta$-lactamase producing strains of *E.coli* may be used, in particular those carrying an R factor for example R TRM. |

Conditions

The reactions were carried out in 1 cm cuvettes at 37° C. in an SP 800 Pye Unicam spectrophotometer. This instrument can carry four sample cuvettes and their corresponding blanks. The first cuvette was used for the control reaction and contained no inhibitor. The 2nd, 3rd and 4th cuvettes were used for various dilutions of the inhibitor. Thus:

| Reagents | Sample Cuvette | Blank Cuvette |
| --- | --- | --- |
| Starch/iodine reagent | 1.0 ml | 1.0 ml |
| *E.coli* $\beta$-lactamase | 0.1 ml | — |

-continued

| Reagents | Sample Cuvette | Blank Cuvette |
| --- | --- | --- |
| Buffer | 0.3 ml | 0.4 ml |
| Inhibitor of buffer | 0.1 ml | 0.1 ml |
| Substrate (added after incubation of above mixtures for 15 mins. at 37° C.) | 1.0 ml | 1.0 ml |

The reactions were followed by recording optical density change at 590 nm. and measuring the velocity of the reaction as optical density change per 100 secs. during the 3–6 minute time interval. The inhibitor sample was diluted until a dilution was reached which gave 50% of the rate of reaction seen in the no-inhibitor control.

DESCRIPTION 2

The KAG Assay

The KAG assay is a method for determining the presence of a $\beta$-lactamase inhibitor in fermentation broths or during stages in the isolation. Molten nutrient agar at 45° C. is seeded with a suitable $\beta$-lactamase producing strain of *Klebsiella aerogenes* and then mixed with a sufficient quantity of a sterile solution of penicillin G to give a concentration of 6 $\mu$g/ml of penicillin G in the agar. The agar is then poured into a petri dish and after solidification equally spaced cylindrical wells are made in the layer of agar by using a sterile metal cutter. The solutions to be tested are introduced into the wells. The dish is then incubated at a constant temperature between 27° C. and 37° C. During the period of incubation, any antibiotic in the test solution diffuses out from the well into the agar and there inhibits the action of $\beta$-lactamase produced by the Klebsiella cells. The penicillin G is thus protected from destruction by $\beta$-lactamase and is present in sufficient concentration to prevent the growth of the Klebsiella. In those parts of the agar to which the antibiotic has not diffused in sufficient concentration, the penicillin G is destroyed by the $\beta$-lactamase, allowing dense growth of the Klebsiella to develop. Clear circular zones of inhibition of Klebsiella growth are thus formed around the wells containing antibiotic the size of each zone depending on the concentration of antibiotic in the solution under test. The potency (arbitrary units/ml) of test solutions is obtained by reference to a standard line of log.conc. antibiotic v. zone diameter. This assay system may also be used for bioautography.

DESCRIPTION 3

Preparation of MM 4550 (Complex) comparable to that disclosed in British Patent No. 1,363,075

*Streptomyces olivaceus* ATCC 21379, was grown for 7 days at 28° C. on a solid agar slant in a Roux bottle. The agar medium had the following composition:

| Constituent | | Amount (g/l) |
| --- | --- | --- |
| Yeast Extract | | 10.0 |
| Glucose Monohydrate | | 10.0 |
| Agar | | 15.0 |
| Tap Water | to | 1 l |

[The "Yeast extract" was "Yeatex" as supplied by Bovril Food Ingredients, P.O. Box 18, Wellington Road, Burton-on-Trent, U.K., and the "Agar" was supplied by Oxoid Limited, Southwark Bridge Road, London, S.E.1., U.K.]

The medium was adjusted to pH 6.8 before sterilisation. 50 ml. of sterile deionised water containing 0.02% Tween 80 [Registered Trade Mark; Tween 80 is a polyoxyethylene sorbitan mono-oleate] was added to a Roux bottle culture and the spores suspended by shaking. This spore suspension was then added as inoculum to 75 l of sterilised seed stage medium in a 100 l stainless steel fermenter. The composition of the seed stage medium was as follows:

| Constituent | Amount (g/l) |
|---|---|
| Soya-bean Flour | 10.0 |
| Glucose Monohydrate | 20.0 |
| Tap Water to | 1 l |

[The "Soya-bean Flour" was Arkasoy 50 as supplied by the British Arkady Co.Ltd., Old Trafford, Manchester].

To control foaming 50 ml. of 10% v/v Pluronic L81 (Registered Trade Mark) in soya-bean oil was added to the fermentation medium before sterilisation. [Pluronic L81 was supplied by Jacobsen van den Berg U.K. Ltd., 231 The Vale, London, W.3., U.K., and is a block polymer of ethylene oxide and propylene oxide].

The medium was steam sterilised in the fermenter for 20 mins at 120° C. The seed stage culture was stirred at 340 r.p.m. with a 8.5 inch diameter vaned disc agitator and supplied with 150 l/min sterile air through an open ended sparger. The culture vessel was fitted with baffles. The temperature was controlled at 28° C. and after incubation under these conditions for 45 hours, 7.5 l of this seed culture was added as inoculum to 150 l sterile fermentation medium in a 300 l stainless steel fermenter. The fermentation medium had the following composition:

| Constituent | Amount (g/l) |
|---|---|
| Soya-bean Flour (Arkasoy 50) | 10.0 |
| Glucose Monohydrate | 20.0 |
| Chalk (Precipitated Calcium Carbonate) | 0.2 |
| Cobalt Chloride (CoCl$_2$,6H$_2$O) | 0.001 |
| Tap Water to | 1 l |

300 ml. of 10% Pluronic L81 in soya-bean oil was added to prevent foaming. The fermentation was harvested after 48 hours and clarified by centrifugation. The clarified brew gave 50% inhibition in the enzyme assay at a dilution of 1 in 100,000. 100 l of the clarified brew was stirred with 12 kg. wet weight of Whatman DE32 (Registered Trade Mark) ion exchange cellulose in the acetate form, [as supplied by H. Reeve Angel & Co., 14 New Bridge Street, London E.C.4, U.K; the material is a microcrystalline cellulose substituted by diethylaminoethyl groups].

The slurry was filtered and the MM 4550 (Complex) was eluted from the cellulose with 12 l of 0.5 M potassium sulphate. The extract was concentrated to 6 l in a climbing film evaporator under vacuum and below 30° C. Much of the potassium sulphate was precipitated by the addition of 12 l of acetone. The solution was filtered and concentrated to 200 ml. by evaporation under vacuum below 30° C. The concentrate was loaded onto a 76 mm×2 m column of Amberlite XAD-4 resin (Registered Trade Mark) [as manufactured by Rohm & Haas Co., Philadelphia, U.S.A.; the material is a non-ionic polystyrene resin[, eluted with deionised water and the elutate was collected in 140 ml. fractions. Active fractions, as detected by the agar diffusion assay were bulked (2.2 l) and concentrated to 275 ml. by ultrafiltration using an Amicon UM-05 membrane (150 mm diameter) (Registered Trade Mark) [as supplied by Amicon Ltd., 57 Queen's Road, High Wycombe] under nitrogen pressure of 60 p.s.i. The concentrate was freeze dried to yield 2.2 g. of brown powder ($I_{50}$ 0.004 μg/ml.). 1 g. of the powder was dissolved in 1 l of 0.2 M sodium sulphate and mixed with 1 l of 2% w/v tetra-n-butylammonium hydrogen sulphate (as supplied by AB Astra, Sodertalje, Sweden) in dichloromethane. The dichloromethane phase was separated by gravity, cooled to −70° C., filtered to remove ice and concentrated by evaporation to 20 ml. 400 ml. of 40°–60° C. petroleum spirit was added to the concentrate and the precipitate collected by centrifugation. The precipitate was redissolved in dichloromethane (10 ml.) and extracted with water (10 ml.) containing barium iodide (80 mg.) and barium carbonate (70 mg.). The phases were separated, the aqueous phase filtered and adjusted to pH 6.5. The solution was freeze dried to yield a yellow powder. The solid was washed with acetone to dissolve out excess barium iodide and the pale yellow solid recovered by centrifugation and dried in vacuo. The yield was 13 mg. ($I_{50}$ 0.0004 μg/ml.).

DESCRIPTION 4

Demonstration of Carbon Adsorption of Culture Filtrate useful in obtaining material as described in British Pat. No. 1,361,075

Culture filtrate obtained as in Description 3 gave a zone diameter of 17 mm in a hole-in-plate agar diffusion antibacterial assay against *Klebsiella aerogenes;* a zone diameter of 38 mm in the KAG assay and $I_{50}$ at a dilution of 1 in 150,000. The clarified culture filtrate (170 l) at 5° C. was percolated by upward flow through a 9" diameter column packed to a height of 16" with active charcoal (Farnell BO, as supplied by Dearborn Chemicals Ltd., Dilton, Widnes, Lancs., 60–80 mesh prewashed with N HCl and buffered at pH 6 with phosphate) at a flow rate of 800–1000 ml/min. Brew was washed from the carbon with deionised water (10 l) and eluted with 20% acetone at 20° C. The active fractions amounting to 10 l were concentrated by evaporation in vacuo, below 30° C. to 6 l and freeze dried to yield 282 g. of crude MM 4550 (Complex) preparation giving an $I_{50}$ of 0.05 μg/ml. The recovery of enzyme inhibitory activity was 22%.

An alternative activated charcoal which gives similar results is Darcogranular carbon (as supplied by Honeywill-Atlas Ltd., Mill Lane, Carshalton, Surrey).

DESCRIPTION 5

Demonstration of Ion Exchange Resin Chromatography of Culture Filtrate useful in obtaining material as described in British Pat. No. 1,363,075

A 1 cm. internal diameter column was packed to a height of 6 cm. (bed volume 4.7 ml.) with Dowex 21K ion-exchange resin (20–50 U.S. mesh, chloride form) (Dowex 21K was supplied by B.D.H. Chemicald Ltd., Poole, Dorset, U.K. and is a polystyrene-divenylbenzene resin containing basic groups). The bed of resin was then washed with approximately 4×4.7 ml. of 5% aqueous methanol, followed by 1×4.7 ml. of distilled water. Two liters of culture filtrate was obtained essentially as described in Description 3. The resin was then washed with 50% aqueous methanol to remove impurities.

The MM 4550 (Complex) was eluted from the resin with 5% NaCl in 50% aqueous methanol. Table 1 below shows the results obtained in terms of units of activity. The MM 4550 (Complex) content of culture filtrate was arbitrarily set at 8 units/ml. The eluted fractions from the column were assayed using an antibacterial diffusion method against Klebsiella aerogenes and the activity units were calculated by reference to a standard line prepared by plotting zone diameter against units/ml. for various dilutions of culture filtrate (i.e. the culture filtrate was used as a standard).

It can be seen that the column was an effective way of concentrating the MM 4550 (Complex). Fractions 2-5 inclusive contained 60% of the activity in a total volume of only 37 ml. The total dry weight of these fractions was about 210 mg. whereas 35 g. of solids had been added to the column.

TABLE 1

RESULTS OF CHROMATOGRAPHY ON DOWEX 21K

| Sample | pH | Volume (ml) | Units/ml | Total units |
|---|---|---|---|---|
| Culture filtrate | 6.5 | 1970 | 8 | 15760 |
| Percolate 1 | 6.9 | 550 | <1 | <100 |
| Percolate 2 | 7.0 | 525 | <1 | <100 |
| Percolate 3 | 7.0 | 595 | <1 | <100 |
| Percolate 4 | 7.0 | 300 | <1 | <100 |
| Eluate 1 | 7.8 | 7.0 | 84 | 588 |
| Eluate 2 | 7.8 | 7.0 | 328 | 2296 |
| Eluate 3 | 7.7 | 8.5 | 440 | 3740 |
| Eluate 4 | 7.7 | 10.0 | 320 | 2200 |
| Eluate 5 | 7.6 | 11.5 | 160 | 1840 |
| Eluate 6 | 7.5 | 11.0 | 80 | 880 |
| Eluate 7 | 7.6 | 14.2 | 66 | 937 |
| Eluate 8 | 7.6 | 20.0 | 33 | 660 |
| | | | Total: | 13141 |

DESCRIPTION 6

Demonstration of Ion-Pair Extraction of Culture Filtrate useful in obtaining material as described in British Pat. No. 1,363,075

Sodium sulphate (248 g.) was added to clarified culture filtrate (10 l) prepared as described in Description 3 and the solution extracted with 2% tetra n-butyl ammonium hydrogen sulphate in dichloromethane (10 l) by stirring for 30 minutes. The phases were separated and the dichloromethane phase cooled to 2° C. A small quantity of suspended water was removed by filtration through Whatman No. 1 PS paper. The dichloromethane solution was concentrated to 20 ml. by evaporation in vacuo below 30° C. The addition of 400 ml. of petroleum ether (40°-60°) precipitated a gum which contained the MM 4550 (Complex).

The gum was collected by centrifugation, redissolved in 50 ml. of dichloromethane and extracted with 50 ml. of water containing 1 g. barium iodide and 1 g. barium carbonate by shaking for 2 minutes. The solids present were filtered off and the two phases separated. The aqueous phase containing the MM 4550 (Complex) as the barium salt was adjusted to pH 6.5 and freeze dried to yield 317 mg. of a crude preparation of MM 4550 (Complex) with an $I_{50}$ of 0.001 μg/ml.

DESCRIPTION 7

Preparation of Partially Purified Antibiotic Complex containing MM 4550A and MM 13902 using Tetra n-butyl Ammonium Hydrogen Sulphate A crude preparation of MM 4550 (Complex) prepared as in was redissolved in water (12.5 g. in 125 ml.) and extracted with 125 ml. of 10% w/v tetra n-butyl ammonium hydrogen sulphate in dichloromethane. The two phases were separated and the dichloromethane back extracted with 100 ml. water at 2° C. containing 190 mg. sodiium iodide by stirring slowly and adjusting the aqueous phase to pH 6.4 with 2% $NaHCO_3$. The solution was freeze dried and the dry solid washed with acetone to yield 88 mg. of a preparation mixed sodium salts of MM 4550A and MM 13902 having an $I_{50}$ of 0.0002 μg against *Escherichia coli* β-lactamase. The recovery of antibiotics was 70%.

The antibacterial activity of mixtures of ampicillin and material prepared as described in Procedure 7 was determined by the serial dilution method in nutrient agar. The minimum inhibitory concentrations which were obtained are given in Table 2.

TABLE 2

SYNERCISM BETWEEN AMPICILLIN AND MM 4550 (COMPLEX)

| | Ampicillin | Ampicillin + MM 4550 (Complex) at | | |
|---|---|---|---|---|
| Organism | Alone | 0.1 μg/ml | 1 μg/ml | 10 μg/ml |
| *E. coli* B11 | >500 | >500 | 500 | 50 |
| *E. coli* JT417 | 250 | 250 | 250 | 50 |
| *E. coli* JT39 | >500 | >500 | 500 | 25* |
| *Shigella sonnei* S239 | 125 | 125 | 125 | 25* |
| *Klebsiella aerogenes* A | 125 | 25 | 5* | <0.1* |
| *Klebsiella aerogenes* IP282 | 50 | 50 | 12.5 | 0.5* |
| *Proteus mirabilis* 889 | >500 | >500 | 50 | 0.5 |
| *Proteus mirabilis* 247 | >500 | 125 | 5.0 | 0.5 |
| *Proteus morganii* F | 50 | 50 | 25 | 0.5 |
| *Proteus rettgeri* R110 | 250 | 125 | 25* | 0.25* |
| *Staph. aureus* (Russell) | 250 | 125 | <0.1 | 0.25 |
| *Staph. aureus* (Russell H) | >500 | <0.1 | <0.1 | <0.1 |

*Partial inhibition by MM 4550 (Complex) alone at these concentrations.
Similar synergistic effects were observed for mixtures of Amoxycillin and MM 4550 (Complex).

DESCRIPTION 8

Preparation of Partially Purified Antibiotic Complex containing MM 4550A and MM 13902 using cetyldimethylbenzylammonium chloride Freeze dried product ($I_{50}$=0.02 μg/ml) from a Farnell carbon column eluted with acetone/water as in Procedure 4 was dissolved in distilled water at a concentration of 13 mg/ml. The solution was adjusted to pH 6.5.

100 ml. of the solution was extracted with an equal volume of 0.1% cetyldimethylbenzylammonium chloride in dichloromethane. The phases were separated by centrifugation and the organic phase back extracted with 100 ml. of 0.05% sodium iodide solution. The phases were separated and any dichloromethane in the aqueous phase removed by maintaining the solution under reduced pressure for 10 minutes.

The aqueous solution was freeze dried and the product of freeze drying washed three times with 50 ml. portions of acetone. The acetone washed product was dried in a vacuum desiccator to yield a light brown powder (4.3 mg; $I_{50}=0.002$ μg/ml).

DESCRIPTION 9

Preparation of Partially Purified Antibiotic Complex containing MM 4550A and MM 13902 using Gel Filtration 1 g. of crude MM 4550 (Complex), $I_{50}$ 0.2 μg/ml, prepared by the method of Description 4 was chromatographed on Sephadex G25 (fine grade), using acetone/water 4:6 v/v as eluant. The column dimensions were 2.5 cm × 32 cm and elution was carried out at 1.5 ml/min. The active fractions were combined, concentrated in vacuo below 30° C. and freeze dried to yield 22 mg. amorphous buff coloured solid having an $I_{50}$ of 0.005 μg/ml. The recovery was 88% and purification 40-fold.

DESCRIPTION 10

Preparation of Purified Antibiotic Complex containing MM 4550A and MM 13902 using Cellulose Chromatography MM 4550 (Complex) (610 mg.) prepared as in Procedure 7 was chromatographed on a 2.5 cm × 32 cm. column of cellulose (Whatman CC 31) and eluted with a mixture of isopropanol/water, 7/3 (v/v) at 1.5 ml/min. The antibacterially active fractions were combined, concentrated in vacuo, below 30° C. and freeze dried to yield 40 mg. of brown amorphous solid preparation of MM 4550 (Complex) I50 of 0.00007 μg/ml. The very small value of the $I_{50}$ indicates that the active material is of improved purity.

On a different occasion the above procedure yielded a material having an $I_{50}$ of 0.001 μg/ml. This material had the antibacterial activity shown in Table 3 when determined by a standard microtitre method in Oxoid sensitivity broth using light inocula (1% of overnight broth).

TABLE 3

ANTIBACTERIAL ACTIVITY OF MIXTURE OF MM 4550A AND MM 13902 HAVING AN $I_{50}$ OF 0.001 μg/ml

| Organism | MIC in μg/ml |
|---|---|
| Staphylococcus aureus (Oxford) | 7.5 |
| Staphylococcus aureus (Russell) | 7.5 |
| Streptococcus faecalis | 125 |
| Bacillus subtilis | 0.9 |
| Escherichia coli (10418) | 3.7 |
| Escherichia coli (B11) | 15 |
| Klebsiella aerogenes | 1.8 |
| Enterobacter cloacae | 62 |
| Proteus mirabilis | 7.5 |
| Providentia stuartii | 7.5 |
| Acinetobacter anitratus | 0.9 |
| Pseudomonas aeruginosa | 250 |
| Serratia marcescens | 7.5 |
| Salmonella typhimurium | 15 |

TABLE 3-continued

ANTIBACTERIAL ACTIVITY OF MIXTURE OF MM 4550A AND MM 13902 HAVING AN $I_{50}$ OF 0.001 μg/ml

| Organism | MIC in μg/ml |
|---|---|
| Shigella sonnei | 7.5 |

DESCRIPTION 11

MM 13902

MM 13902 may be recognised by its properties which are as follows: MM 13902 is an acidic solid which in the form of a sodium salt has the following characteristics:

i. It is highly soluble in water, soluble in methanol and substantially insoluble in chloroform, diethyl-ether and hydrocarbons.

ii. In aqueous solution, it has a characteristic ultra-violet spectrum with absorption maxima one of which is at about 305 nm.

iii. When present at 0.4% w/w in a freshly prepared KBr, disc, it has a characteristic infra-red spectrum which has absorption maxima at inter alia about 3450, 2950, 1750, 1620, 1510, 1400 and 1260 cm$^{-1}$.

iv. It has a characteristic n.m.r. spectrum when taken in $D_2O$ which spectrum possesses inter alia (a) a pair of low field doublets centred at approximately 2.85τ and 4.00τ with coupling constants of approximately 14 Hz; (b) a doublet centred at approximately 8.55τ and (c) a sharp singlet at approximately 8.00τ.

v. It possesses antibacterial activity against various species including inter alia, strains of Staphylococcus aureus, Bacillus subtilis, Escherichia coli, Klebsiella aerogenes, Proteus mirabilis, Salmonella typhi and Pseudomonas aeruginosa.

vi. When mixed with ampicillin it synergyses its activity against organisms including strains of Escherichia coli, Klebsiella aerogenes, Proteus mirabilis, Proteus morganii and Staphylococcus aureus Russell.

The pure di-sodium salt of MM 13902 has an $I_{50}$ (as hereinbefore described) of between 0.001 μg/ml and 0.0001 μg/ml against the β-lactamase of Escherichia coli B 11.

When run on cellulose in a thin layer chromatography system the pure di-sodium salt of MM 13902 has the following approximate $R_f$ values:

(a) n-butanol/isopropanol/water—7:7:6 v/v; $R_f=0.85$
(b) isopropanol/water—7:3 v/v; $R_f=0.70$
(c) n-butanol/ethanol/water—7:7:6; $R_f=0.79$
(d) n-propanol/water—4:1; $R_f=0.68$

DESCRIPTION 12

Organisms

The property of producing MM 4550 (Complex) was first discovered in the cultures ATCC 21379, ATCC 21380, ATCC 21381 and ATCC 21382 which had been isolated from soil samples obtained from Spain, New Zealand, South Africa and Isreal respectively. In the laboratory, these cultures appeared identical and all were identified as Streptomyces olivaceus, by Dr. Bousfield, the actinomycete expert at the National Collection of Industrial Bacteria (NCIB), Torry Research Station, Aberdeen, Scotland, using the widely accepted 1967 classification of Hütter [Systematic der Streptomyceten, S. Karger, Basel, 382 pp]. MM 4550A production has since been found in other streptomyces species as may be seen from Table 5.

S. olivaceus was first described by Waksman in 1919 [Cultural Studies of Species of Actinomyces, Soil. Sci., 8,71–215]. Subsequently, in 1960, a group of Russian workers described a species with very similar characteristics but which they named *Actinomyces (Streptomyces) fulvoviridis*. [Kuchaeva et al., Trud. Inst. Mikrobiol., Akad Nauk. SSSR., 8, 226–253 (1960)].

Micro-organisms of the genus Streptomyces are extremely variable in their morphological and physiological characteristics depending on the conditions under which they are grown. Descriptions of many species had been published before the existence of this extreme variability had been recognised, with consequent duplication and synonymy. Hütter (1967) lists 25 species as being synonymous with *S. olivaceus* including *S. fulvoviridis*. To resolve the confusion in nomenclature and classification, the International Streptomyces Project was begun in 1962, Shirling et al., Int. J. Syst. Bacteriol, 18, 69–189 (1968). Collaborators in this Project have carried out a series of studies aimed at producing accurate descriptions of species of Streptomyces under standard conditions. In this scheme, standard descriptions have been produced of type strains of some 400 named species including *Streptomyces olivaceus* and *Streptomyces fulvoviridis*.

The I.S.P. description of *S. olivaceus* and *S. fulvoviridis* differ in two characters only: (i) the form of the sporophore and (ii) ability to utilise inositol as sole carbon source.

*S. olivaceus* is described as follows:

Spore chain morphology: Section Spirales, with open spirals intergrading through flexuous spore chains suggestive of Section Rectiflexibiles. Mature spore chains generally long, often with more than 50 spores per chain.

Carbon utilisation: D-Glucose, L-arabinose, D-xylose, i-inositol, D-mannitol, D-fractose and rhamnose are utilised for growth. No growth or only trace of growth on sucrose and raffinose.

*S. fulvoviridis* is described as follows:

Spore chain morphology: Section Rectiflexibiles. Mature spore chains moderately short with 10–50 spores per chain. Carbon utilisation: D-Glucose, L-arabinose, D-xylose, D-mannitol, D-fructose and rhamnose are utilised for growth; utilisation of sucrose is doubtful. No growth or only trace of growth on i-inositol or raffinose.

Characterisation of a number of cultures named or synonymous with *S. olivaceus* or *S. fulvoviridis* and other related species was determined using the standard methods and media (Shirling et al., Int. J. Syst. Bacteriol, 16, 313-340, (1966) recommended in the International Streptomyces Project (ISP).

The cultures were derived from different sources. ATCC 21379, 21380, 31381, 21382 were isolated from soil on the basis of producing MM 4550 (Complex). The other strains were obtained from various culture collections for comparison purposes.

Results of the tests for production of MM 4550 (Complex), colour of aerial mycelium, sporophore shape, colour of substrate mycelium soluble pigment production, melanin production and carbon source utilisation are given in Tables 4–8. For all strains the spore surface, as seen by electron microscopy, is smooth.

From the ISP description it is clear that the spiral growth of the sporophore in *S. olivacous* is a variable character. True spirals were observed with a variable frequency in the type species of *S. olivaceus*, i.e. ATCC 3335. The majority of the sporophores were long. No true spirals were observed from the cultures ATCC 21379, 21380, 21381 or 21382 although the sporophores were long and showed a tendency to spiral among a background of Rectiflexibiles types. However, in two *S. olivaceus* strains, NCIB 8238 and NCIB 8509, the majority of sporophores were of the Rectiflexibiles type. In NCIB 8238 they were of medium length while those of NCIB 8509 were long.

The sporophores observed from ATCC 15863, the type species of *S. fulvoviridis*, were shorter than those seen from isolates ATCC 21379, 21380, 21381 and 21382 and were only of the Rectiflexibiles types. In respect of this character therefore, the isolates ATCC 21379, 21380, 21381 and 21382 correspond fairly well but not exactly with the *S. olivaceus* description.

Isolates ATCC 21379, 21380, 21381 and 21382 show some variability with regard to inositol utilisation which is the other differentiating character according to the I.S.P. type species descriptions between the species *S. olivaceus* and *S. fulvoviridis* (Table 8). ATC 31126 and ATCC 21380 utilise inositol, which is characteristic of *S. olivaceus*, while the other strains show doubtful or negative utilisation. However, it is not generally considered satisfactory to separate off a species on the basis of the ability to utilise a single carbohydrate. Such a difference might arise by a single gene mutation and is often considered to be of strain significance only. The difference in sugar utilisation by the *S. olivaceus* strains NCIB 8138, NCIB 8509, ATCC 21549, ATCC 12019 and ATCC 3335 suggest that many authorities do not consider them of species significance. Thus it is likely that ATCC 21379, 21380, 21381 and 21382 are properly designated *S. olivaceus*.

Unless further studies uncover more important differences between those cultures presently named *S. olivaceus* and *S. fulvoviridis*, it is possible that they will eventually be internationally recognised as a single species. In this case the correct name will be *S. olivaceus*, and this will also include those cultures listed by Hütter as synonymous with *S. olivaceus*.

Examination of culture filtrates of the strains of *S. olivaceus* and related species for the production of MM 4550 (Complex) may be carried out as follows:

Culture filtrates of the listed strains were spotted on Whatman No.1 paper strips at 20 µl per origin and chromatographed in n-butanol/isopropanol/water (7:7:6) overnight in the cold. Another set of strips were run in n-butanol/glacial acetic acid/water (12:3:5) also in the cold overnight. A partially purified sample of MM 4550 (Complex) was also run in the two systems at the same time as a market.

Alternatively, it is possible to extract 25 ml of clarified brew with 12.5 ml of 0.2% cetylbenzylammonium chloride in dichloromethane, separate the phases, retain the organic phase, add 2.5 ml of sodium iodide solution (0.5%), shake, separate the phases, retain the aqueous phase and use this chromatographically, for example, by spotting 5µ onto thin layer chromatography strips and run in n-butanol/isopropanol/water, 7:7:6.

TABLE 5

ABILITY OF CULTURES STREPTOMYCES OLIVACEUS STREPTOMYCES FULVOVIRIDIS AND RELATED SPECIES TO PRODUCE MM 4550 (COMPLEX)

| Culture | | MM 4550 (complex) Production |
|---|---|---|
| Streptomyces olivaceus | ATCC 21379 | + |
| " | ATCC 31126 | + |
| " | ATCC 21380 | + |
| " | ATCC 21381 | + |
| " | ATCC 21382 | + |
| " | NCIB 8238 | + |
| " | NCIB 8509 | + |
| Streptomyces flavovirens | ATCC 3320 | + |
| Streptomyces flavus | ATCC 3369 | + |
| Streptomyces fulvoviridis | ATCC 15863 | + |
| Streptomyces argenteolus | ATCC 11009 | + |
| Streptomyces sioyaerisis | ATCC 13989 | + |
| Streptomyces lipmanii | ATCC 27397 | + |

(Streptomyces olivaceus ATCC 21549, ATCC 12019 and ATCC 3335 did not produce MM 4550 (complex); ATCC 15863 has also been deposited as RIA 660)

TABLE 8

STREPTOMYCES OLIVACEUS, STREPTOMYCES FULVOVIRIDIS AND RELATED SPECIES - PRODUCTION OF PIGMENTS IN CULTURE MEDIA

| Culture | Soluble Non-Melanoid Pigments | | | | *Melanin Production |
|---|---|---|---|---|---|
| | SS | YM | GA | OM | |
| ATCC 21379 | − | − | − | + slight yellow | − |
| ATCC 31126 | − | − | − | − | − |
| ATCC 21380 | − | − | − | − | − |
| ATCC 21381 | − | − | − | − | − |
| ATCC 21382 | − | − | − | − | − |
| NCIB 8238 | + slight brown | − | + slight brown | + slight brown | − |
| NCIB 8509 | − | − | − | + slight yellow | − |
| ATCC 21549 | − | + slight brown | + slight red/brown | + slight brown | − |
| ATCC 12019 | − | − | − | − | − |
| ATCC 3335 | − | − | − | − | − |
| ATCC 15863 | − | − | − | − | − |
| ATCC 3320 | + | − | − | − | − |

TABLE 6

STREPTOMYCES OLIVACEUS, STREPTOMYCES FULVOVIRIDIS AND RELATED SPECIES - COLOUR AND MORPHOLOGY OF MATURE SPORULATING AERIAL MYCELIUM ON ISP MEDIA AFTER 14 DAYS GROWTH

| Culture | SS | YM | GA | OM | Sporophore Morphology mid size |
|---|---|---|---|---|---|
| ATCC 21379 | Grey | Grey | Grey/White | Grey | Long RF |
| ATCC 31126 | Grey/Brown | Grey/Brown | Grey | Grey | Long RF |
| ATCC 21380 | Grey | Grey | Grey | Grey | Long RF |
| ATCC 21381 | Grey | Grey | Pale Grey | Grey/White | Long RF |
| ATCC 21382 | Grey/White | Grey | Grey | Grey | Long RF |
| NCIB 8238 | Grey/White | Grey | Grey | Grey | Medium RF |
| NCIB 8509 | Grey | Grey | Grey | Grey | Long RF |
| ATCC 21549 | Grey | Grey | Grey | Grey | Long S |
| ATCC 12019 | Grey | Grey | Grey | Grey | Long RF/S |
| ATCC 3335 | Grey | Grey | Grey | Grey | Long RF/S |
| ATCC 15863 | Grey/White | Grey | Grey/White | Grey | Medium RF |
| ATCC 3320 | Grey/blue | Grey | Grey/Green | Grey | Long RF |
| ATCC 3369 | Grey | Grey | Grey | Pale grey/brown | Medium RF/RA |
| ATCC 11009 | Pale Grey | Grey/brown | Grey/White | Grey/Green | Medium RF/RA |
| ATCC 13898 | White/Grey | White | White/yellow | Grey/White | Short S |

SS = Inorganic salts - starch agar (ISP Medium 4)
YM = Yeast extract - malt extract agar (ISP Medium 2)
GA = Glycerol - asparagine agar (ISP Medium 5)
OM = Oatmeal agar (ISP Medium 3)
RF = Rectiflexibiles
RA = Retinaculiaperti
S = Spirales

TABLE 7

STREPTOMYCES OLIVACEUS, STREPTOMYCES FULVOVIRIDES AND RELATED SPECIES - COLOUR OF SUBSTRATE MYCELIUM AS VIEWED FROM THE REVERSE SIDE

| Culture | SS | YM | GA | OM |
|---|---|---|---|---|
| ATCC 21379 | Olive | olive brown | grey/brown | olive green |
| ATCC/31126 | olive brown | olive brown | brown | olive brown |
| ATCC 21380 | olive | olive green | olive brown | olive yellow |
| ATCC 21381 | dark brown | dark brown | olive green | olive green |
| ATCC 21382 | olive | olive | brown | olive green |
| NCIB 8238 | brown | olive/brown | brown | olive yellow |
| NCIB 8509 | brown | olive | olive brown | olive yellow |
| ATCC 21549 | buff/black | brown/black | brown/black | buff/grey |
| ATCC 12019 | buff | buff | buff | buff |
| ATCC 3335 | brown | brown | brown | grey |
| ATCC 15863 | brown/grey | dark brown | olive brown | olive yellow |
| ATCC 3320 | yellow/brown | olive/brown | olive/brown | orange/brown |
| ATCC 3369 | buff/grey | yellow brown | buff/green | yellow |
| ATCC 11009 | black | black/yellow | black/yellow | grey/green |
| ATCC 13989 | Orange | yellow | yellow | colourless |

TABLE 8-continued
STREPTOMYCES OLIVACEUS, STREPTOMYCES FULVOVIRIDIS AND RELATED SPECIES - PRODUCTION OF PIGMENTS IN CULTURE MEDIA

| Culture | Soluble Non-Melanoid Pigments | | | | *Melanin Production |
|---|---|---|---|---|---|
| | SS | YM | GA | OM | |
| ATCC 3369 | slight pink | − | − | − | − |
| ATCC 11009 | − | + slight brown | − | − | − |
| ATCC 13989 | − | + slight orange | − | − | − |

+ = Pigment produced
− = Pigment not produced
* Tested on peptone-yeast-iron agar (ISP6), tyrosine agar (ISP17) and tryptone-yeast broth (ISP 1)

TABLE 9
STREPTOMYCES OLIVACEUS, STREPTOMYCES FULVOVIRIDIS AND RELATED SPECIES - CARBON UTILISATION TESTS

| Culture | Rhamnose | Raffinose | Sucrose | Inositol | Glucose | Xylose | Fructose | Marmitol | Arabinose |
|---|---|---|---|---|---|---|---|---|---|
| ATCC 21379 | + | − | − | ± | + | + | + | + | + |
| ATCC 31126 | + | − | − | + | + | + | + | + | + |
| ATCC 21380 | + | − | − | + | + | + | + | + | + |
| ATCC 21381 | + | − | − | − | + | + | ± | ± | + |
| ATCC 21382 | + | + | − | − | + | + | + | + | + |
| NCIB 8238 | + | − | − | − | + | + | + | + | + |
| NCIB 8509 | + | ± | − | − | + | + | + | ± | + |
| ATCC 21549 | − | − | − | + | + | + | + | + | + |
| ATCC 12019 | + | ± | + | + | + | + | + | + | + |
| ATCC 3335 | + | − | ± | + | + | + | + | + | + |
| ATCC 15863 | + | − | − | − | + | + | + | + | + |
| ATCC 3320 | + | − | ± | − | + | + | + | + | + |
| ATCC 3369 | + | − | ± | ± | + | + | + | + | + |
| ATCC 11009 | + | − | − | + | + | + | + | + | + |
| ATCC 13989 | − | + | + | + | + | + | + | + | − |

+ denotes the compound is utilised
− denotes the compound is not utilised
± denotes utilisation is doubtful or very poor

EXAMPLE 1
Preparation of MM 4550 (Complex) and Separation into MM 4550A and MM 13902

The isolation procedures detailed in the Description section may be utilized in a variety of sequences. A particularly suitable sequence is carbon adsorption, ion pair extraction and cellulose chromatography as described below:

Culture filtrate (340 l) (obtained as in Description 3) was percolated by upward flow at 800–1200 ml/min. through a column (9" diameter×21" high) packed with Farnell BO carbon. The carbon had been used before for adsorption of Mm 4550 (Complex) and was regenerated by washing with the following reagents:

0.5 N NaOH; 0.2 N NaOH/acetone (3:2); water; N HCl;
water; phosphate buffer pH 6; water.

The column was washed with water (20 l) to displace the culture filtrate and eluted by downward flow with acetone/water 2:8 v/v at 200–250 ml/min. One liter fractions were collected. Fractions containing the MM 4550 (Complex) as determined by an antibacterial diffusion assay using *Klebsiella aerogenes* were combined (11 l) and concentrated by evaporation in vacuo below 30° C. to 5.5 l. The recovery of MM 4550 (Complex) at this stage was 20%.

The concentrate was cooled to 2° C., 5.5 l of 2% w/v tetra n-butyl-ammonium hydrogen sulphate in dichloromethane at −5° C. was added and the two phases mixed together for 2 minutes. The dichloromethane phase was separated and added to one liter of sodium iodide solution (0.6%) at 0° C. The two phases were stirred gently and the aqueous phase gradually adjusted to between pH 6.5–7.0 with 2% aqueous solution of $NaHCO_3$. The aqueous phase was separated and freeze dried. The dried solid was extracted with dry acetone to dissolve out excess sodium iodide and the acetone removed from the insoluble residue in vacuo, to yield a buff coloured powder (1.1 g.). Overall recovery of MM 4550 (Complex) at this stage was 10%. The purification calculated on total dissolved solids in the culture filtrate was 125-fold.

A 2.5 cm. diameter column was packed with cellulose powder (Whatman CC 31) in isopropanol/water, 7:3 v/v, to a height of 32 cm. 500 mg. of the buff powder was dissolved in 2 ml. isopropanol/water 7:3 v/v and chromatographed using the same solvent at a flow rate of 1.5 ml/min. Fractions (3 ml.) were collected from the column and those showing UV absorption maxima at about 285 nm. were combined, concentrated and freeze dried to yield MM 4550 (Complex). Previous experiments have established that fractions absorbing at about 285 nm. contained enzyme inhibiting, antibacterially active material.

The yield of freeze dried MM 4550 (Complex) was 35 mg. It had a brown amorphous appearance and an $I_{50}$ of 0.0001 μg/ml. The recovery of active material at this stage was 3% overall and the purification 600-fold overall.

The antibacterial activity of this preparation was determined by the standard Microtiter method in Oxoid sensitivity test broth using light inocula. The resulting minimum inhibitory concentrations were similar to those shown in Table 3 hereinbefore.

Analysis of the preparation by thin layer chromatography on cellulose (Eastman Kodak "Chromagram" sheets) developed with n-butanol; isopropanol:water (7:7:6) separated two active substances, one with an approximate $R_f$ of 0.54 which was designated MM 4550A and one with an approximate $R_f$ of 0.72 which was designated MM 13902. Both these materials may be detected by bioautography on a variety of organisms including *B. subtilis, Staphylococcus aureus* (Oxford), *Staphylococcus aureus* (penicillin resistant), *Escherichia coli* (penicillin sensitive and resistant), *Salmonella typhimurium, Proteus mirabilis, Proteus morganii* and *Klebsi-*

*ella aerogenes.* Some of the results obtained are summarized in Table 4.

In a further experiment, the two substances were separated on a cellulose thin layer developed with isopropanol:water (8:2) and extracted from the cellulose with phosphate buffer. Each extract was assayed for β-lactamase inhibition and both substances were shown to be inhibitors of *Escherichia coli* β-lactamase. Both substances were also shown to be synergistic with benzylpenicillin against *Klebsiella aerogenes.*

TABLE 4
ANTIBACTERIAL ACTIVITY OF MM 4550A AND MM 13902 AS DETERMINED BY BIOAUTOGRAPHY (TLC WITH CELLULOSE AND BUTANOL/ISOPROPYL ALCOHOL/WATER 7:7:6 v/v)

| Organism | Zone Diameter on Bioautography | |
|---|---|---|
| | MM 4550A zone in mm at $R_f$ 0.58 | MM 13902 zone in mm at $R_f$ 0.70 |
| Klebsiella aerogenes | 20.0 mm | 20.0 mm |
| Proteus mirabilis | 17.5 mm | 13.5 mm |
| Proteus morganii | 16.0 mm | 9.5 mm |
| Salmonella typhi | 19.5 mm | 21.0 mm |
| Escherichis coli 10418 | 20.0 mm | 13.5 mm |
| Escherichia coli 311 | 17.5 mm | 10.5 mm |
| Enterobacter aerogenes | 6.5 mm | No Zone |
| Staphylococcus aureus (Oxford) | 13.0 mm | 4.0 mm |
| Staphylococcus aureus (Russell) | 12.0 mm | 4.0 mm |
| Bacillus subtilis | 24.0 mm | 15.0 mm |

EXAMPLE 2

Preparation of MM 4550 (Complex) and Separation into MM 4550A and MM 13902

Culture filtrate (1100 l) from the fermentation of *Streptomyces olivaceua* ATCC 31126 at pH 6.5 and 5° C. were percolated at 3.2 l/min. through a column (0.3 m × 1 m) packed with Darco granular carbon. [The carbon had already been used for adsorption of MM 4550 (Complex) and was regenerated before use by washing with the following reagents:

0.5 N NaOH; 0.2 N NaOH/acetone (3:2); water; N HCl; water; phosphate buffer, pH 6; water].

The column was washed with water (60 l) to displace the culture filtrate eluted with acetone/water (2:8 v/v) at 30° C. at 1.1 l/min. 60 l was collected followed by 5 × 10 l fractions. Those fractions containing the MM 4550 (Complex), as determined by the antibacterial diffusion assay using *Klebsiella aerogenes* were pooled (40 l) and concentrated in vacuo below 30° C. to 32 l. The recovery of MM 4550 (Complex) at this stage was 15%.

The concentrate was cooled to 5° C., 16 l of 0.2% cetyldimethylbenzylammonium chloride in dichloromethane at 5° C. was added and the two phases mixed for 5 mins. The dichloromethane phase was separated and added to 3.75 l sodium iodide solution (0.4%) at 5° C. The two phases were mixed for 5 mins., the aqueous phase was separated and freeze dried. The dry solid was extracted with dry acetone to dissolve out excess sodium iodide and the residual solid was dried in vacuo to yield a buff coloured powder (2.87 g). Overall recovery of MM 4550 (Complex) at this stage was 6%. The purification calculated on total dissolved solids in the culture filtrate was 160-fold.

A 63 mm diameter column was packed with cellulose powder (Whatman CC 31) in isopropanol-water (7:3 v/v) to a height of 300 mm. 2.0 g. of the buff coloured powder was dissolved in 5 ml. isopropanol/water (7:3 v/v) and chromatographed in the same solvent at 3 ml/min. Fractions containing MM 4550 (Complex), as determined by assay against *Klebsiella aerogenes* were pooled, concentrated by evaporation in vacuo below 30° C. and freeze dried to yield a brown solid (207 mg.). The recovery of MM 4550 (Complex) for this stage was 51% and the purification was 5-fold.

A 16 mm. diameter column was packed with cellulose powder (Whatman CC 31) in n-propanol/water (4:1 v/v) to a height of 300 mm. 198 mg. of the brown solid was dissolved in water/n-propanol (1:1) and chromatographed in n-propanol/water (4:1 v/v) at a flow rate of 0.5 ml/min. Fractions (6 ml.) were collected, bioassayed against *Klebsiella aerogenes* and the uv spectrum of each fraction measured. Fractions 23-28, having a uv maximum at about 305 nm, contained the disodium salt of MM 13902. These fractions were pooled, concentrated under vacuum and freeze dried to give 30 mg. of solid. This preparation showed only one zone of antibiotic activity at $R_f$ 0.77 on thin layer chromatography using Eastman Kodak cellulose plates with n-propanol/water (4:1 v/v). The zone was detected by bioautography on *Bacillus subtilis.* Fractions 29-40, having a uv absorption maximum at about 285 nm, contained MM 4550A. They were combined, concentrated under vacuum and freeze dried to give 53 mg. of solid which contained a salt of MM 4550A contaminated with a small quantity of a salt of MM 13902.

EXAMPLE 3

A Preferred Isolation Procedure for the Preparation of MM 4550 A

A stock of spores of S.olivaceus ATCC 31126 was maintained by storage in tubes of dry soil in a closed container with a dessicant at a temperature of 20° C. A small quantity of soil stock (approximately 20 mg) was transferred aseptically to a 500 ml Erlenmeyer flask containing 100 ml of the following medium:

| Constituent | Amount (g/liter) |
|---|---|
| Glucose monohydrate | 20.0 |
| Soya-bean flour | 10.0 |
| Deionised water to | 1 liter |

The pH was adjusted to 6.5 before sterilisation. The soya bean flour was 'Arkasoy 50' as supplied by British Arkady Co. Ltd., Old Strafford, Manchester, England.

The flask was incubated on a rotary shaker (240 r.p.m.) for about 30 hours at 28° C. 2 ml of the resulting vegetative growth was then used to inoculate a solid agar slant in a Roux bottle. The agar medium had the following composition:

| Constituent | Amount |
|---|---|
| V-8 vegetable juice | 20.0 ml |
| Agar | 20.0 g |
| Deionised water to | 1 liter |

The pH was adjusted to 6.0 before sterilisation. (V-8 juice is obtainable from Campbell's Soups Ltd., Kings Lynn, Norfolk, England).

The inoculation was spread on the agar surface by rocking the bottle which was then incubated upright at 30° C. After two days incubation, surplus liquid in the bottle was removed by pipette and incubation continued for a further 4 days.

It had been previously found that the development of actinophage in the slant culture is suppressed if this method of preparation of the Roux bottle culture is adopted.

50 ml of sterilised deionised water containing 0.02% Tween 80 was added to a Roux bottle culture and the spores suspended by shaking. This spore suspension was then added as inoculum to 75 liters of sterilised seed stage medium in a 100 liter stainless steel fermenter. The composition of the seed stage medium was as follows:

| Constituent | Amount (g/l) |
|---|---|
| Soya-bean flour ('Arkasoy 50') | 10.0 |
| Glucose monohydrate | 20.0 |
| Tap water to | 1 liter |

To control foaming, 50 ml of 10% v/v 'Pluronic L81' in soyal-bean oil was added to the fermentation medium before sterilisation.

The medium was steam sterilised in the fermenter for 20 minutes at 120° C. The seed stage culture was stirred at 140 rpm with a 7.5 inch diameter vaned disc agitator and supplied with 75 liters/min sterile air through an open ended sparger.

The temperature was controlled at 28° C. and after incubation under these conditions for 48 hours the contents of the vessel were added as inoculum to 1500 liters of sterile fermentation medium in a 2000 liter stainless steel fully baffled fermenter. The fermentation medium had the following composition:

| Constituent | Amount (g/liter) |
|---|---|
| Soya-bean flour ('Arkasoy 50') | 10.0 |
| Glucose monohydrate | 20.0 |
| Chalk (precipitated calcium carbonate) | 0.2 |
| Cobalt chloride ($COCl_2 . 6H_2O$) | 0.001 |
| Sodium sulphate (anhydrous) | 1.0 |
| Tap water to | 1500 liters |

The pH was adjusted to 6.0 with sodium hydroxide before sterilisation. 3 liters of 10% 'Pluronic L81' in soya bean oil was added before sterilisation to prevent foaming. After sterilisation the pH was again adjusted, to 7.0, with sterile sodium hydroxide solution. The fermentation was stirred at 106 r.p.m., the stirrer shaft being fitted with two 19 inch diameter vaned disc impellers. Temperature was controlled at 30° C. and airflow at 1200 liters/min. The fermentation was harvested after 60 hours and clarified by centrifugation.

The material produced above was arbitrarily assigned an activity of 340 l/ml. Assays were determined as described in Description 3.

Culture filtrate (1050 l; 340 units/ml.) at 10° C. and pH8 was extracted with dichloromethane (310 l.) at 10° C. containing cetyldimethylammonium chloride (1200 g.) by pumping the two liquids at predetermined flow rates through an in-line mixer. The phases were separated in a Sharples continuous centrifuge having been admixed for about two minutes. The dichloromethane phase (300 l) was back extracted with aqueous sodium iodide. The back extraction was performed in four batches using a total of 7 l water containing 210 g. sodium iodide. The phases were separated by gravity. The aqueous phase was adjusted from pH 7.7 to pH 7.0 with hydrochloric acid and filtered. The sodium iodide extract (7 l) contained 21,900 units/ml.

An ion exchange column was prepared by packing QAE Sephadex A25 (obtained from Pharmacia Ltd.) in pH7 phosphate buffer (0.05 M) containing sodium chloride (0.3 M) into a 10 cm diameter glass column to a height of 40 cm. The sodium iodide extract (7 l) at 5° C. was percolated through the QAE Sephadex at 50 ml./min. The column was eluted with 0.7 M NaCl in 0.05 M phosphate buffer, pH 7 also at 5° C. at a flow rate of 25 ml/min. 2 l eluate was discarded and 90 fractions (100 ml.) were collected. The fractions were scanned in a u.v. spectrophotometer and those fractions showing an absorption maximum at about 285 nm were pooled and adjusted to pH 7 (fractions 25–35, pooled volume 1230 ml. 71,000 units/ml. It had previously been shown that fractions having a maximum in this region containied MM 13902.

Sodium chloride (5 g./100 ml.) was added to the pooled fractions which were then percolated at 5° C. through a 6.3 cm diameter column packed with Amberlite XAD 4 resin (as supplied by Rohm & Haas Ltd.) to a height of 30 cm. at a flow rate of 20 ml./min. The antibiotics were adsorbed to the resin under these conditions whereas the inorganic impurities were not. The antibiotics were eluted at room temperature with distilled water (200 ml.) followed by 50% aqueous methanol. The eluate (1 l) was evaporated below 30° C. under reduced pressure to 70 ml., adjusted to pH 7 and freeze dried to a brown solid (2.18 g.) which was a partially purified salt of MM 4550 A with an activity of 3.100 units/mg.

Partially purified MM 4550 Adi-sodium salt (0.55 g) was chromatographed on a cellulose column (4.5 cm.×29 cm; Whatman CC31 cellose) eluted with n-propanol/water (4:1 v/v) at a flow rate of 2.5 ml./min. The first 135 ml of eluate was discarded and then 15 ml fractions collected. The fractions containing MM 4550A di-sodium salt as determined by uv absorption were pooled 90 ml.), evaporated below 30° C. under reduced pressure to remove n-propanol and freeze dried to yield a yellowish powder (87 mg.) with an activity of 6,600 units/mg. The above material showed a uv absorption maximum at about 285 nm with an $E_1\,_{cm}^{1\%}$ of about 240. This material had the i.r. and n.m.r. spectra shown in FIGS. 2 and 3 respectively. The antibacterial activity of the material is shown in Table 10. Elemental analysis of this material indicated that it contained inter alia nitrogen, sulphur and sodium probably in the ratio N:S:Na–2:2:2. The positive and negative maxima of the circular dichroism curves for di-sodium MM 4550A were determined on a Cary-61 recording spectropolarimeter at concentrations of 0.37 mg/ml at a path length of 1 cm; the results were as follows:

| λ (nm) | Δ $E/m$ |
|---|---|
| 185 | $+2.4 \times 10^{-2}$ |
| 207 | $-1.22 \times 10^{-2}$ |
| 259 | $-2.20 \times 10^{-2}$ |
| 290 | $-1.89 \times 10^{-2}$ |

TABLE 10

ANTIBACTERIAL ACTIVITY OF THE DI-SODIUM SALT OF MM 4550A
(MICROTITRE METHOD - HEAVY INOCULUM, 1/100 OVERNIGHT BROTH)

| Organism | MIC (µg/ml) |
|---|---|
| Bacillus subtilis A | 25 |
| Staph. aureus Oxford | 20 |
| Staph. aureus Russell | 20 |
| Strep. faecalis | 100 |
| Enterobacter cloacae N1 | 100 |
| Kleb. aerogenes A | 2.5 |
| Proteus mirabilis 13 | 10 |
| Proteus vulgaris WO 90 | 5 |
| Prov. stuartii | 5 |
| Ps. aeruginosa A | >100 |
| Salmonella typhimurium CT 10 | 5 |
| Serratia marcescens US 39 | 20 |
| Shigella sonnci | 5 |

What is claimed is:

1. A pharmaceutical composition useful for treating bacterial infections in humans and animals which comprises a synergistically effective amount of a pharmaceutically acceptable di-basic salt of MM 4550A which is at least 70% pure and an antibacterially effective amount of amoxycillin which substance MM4550A is a solid carboxylic acid of the molecular formula $C_{13}H_{16}O_9N_2S_2$ which in the form of a substantially pure sodium salt has the following characteristics:
    (a) in aqueous solution, it has a characteristic ultraviolet spectrum with absorption maxima at about 238 nm and at about 287 nm;
    (b) when present at 0.4% w/w in a freshly prepared KBr disc, it has a characteristic infra-red spectrum substantially as shown in FIG. 2 and has absorption maxima at inter alia about 3450, 2950, 1765, 1695, 1510, 1390 and 1260 cm$^{-1}$;
    (c) it has a characteristic n.m.r. spectrum which when taken in $D_2O$ is substantially as shown in FIG. 3, which spectrum possesses inter alia (i) a pair of low field doublets centred approximately at 2.45τ and 3.65τ with coupling constants of approximately 15 Hz; (ii) a doublet centred at approximately 8.55τ; and (iii) a sharp singlet at approximately 7.95τ;
    (d) it possesses antibacterial activity against various species including inter alia, strains of *Staphylococcus aureus, Bacillus subtilis, Escherichia coli, Klebsiella aerogenes, Proteus mirabilis, Acinetobacter anitratus, Serratia marcescens* and *Shigella sonnei;*
    (e) it synegizes the antibacterial activity of ampicillin against certain β-lactamase producing bacteria including stains of *Escherichia coli, Klebsiella aerogenes, Proteus mirabilis,* and *Staphylococcus aureus Russell;* and
    (f) it is not a polypeptide or protein, in combination with a pharmaceutically acceptable carrier, said di-basic salt of MM 4550A and said *amoxycillin* being present in the ratio of 10:1 to 1:10.

2. A pharmaceutical composition accordfng to claim 1 wherein the ratio is from 3:1 to 1:3.

3. A pharmaceutical composition according to claim 1 wherein the pharmaceutically acceptable di-basic salt of MM 4550A is at least 80% pure.

4. A pharmaceutical composition according to claim 3 wherein the pharmaceutically acceptable di-basic salt of MM 4550A is at least 90 to 100% pure.

5. A pharmaceutical composition according to claim 1 wherein the pharmaceutically acceptable di-basic salt of MM 4550A is in the form of an alkali metal salt.

6. A pharmaceutical composition according to claim 1 wherein the pharmaceutically acceptable di-basic salt of MM 4550A is the sodium, potassium, calcium, magnesium, aluminum or ammonium salt.

7. A pharmaceutical composition according to claim 1 wherein the pharmaceutically acceptable di-basic salt of MM 4550A is in the form of the di-sodium salt.

8. A pharmaceutical composition according to claim 1 wherein the pharmaceutically acceptable di-basic salt of MM 4550A is in the form of the di-potassium salt.

9. A pharmaceutical composition according to claim 1 in oral administration form.

10. A pharmaceutical composition according to claim 1 in parenteral administration form.

11. A pharmaceutical composition according to claim 1 in topical administration form.

12. A composition according to claim 1 which contains amoxycillin or the acetoxymethyl, pivaloyloxymethyl or phthalidyl ester thereof.

13. A composition according to claim 1 in unit dosage form wherein each dosage unit contains 50 to 1,500 mg of a pharmaceutically acceptable di-basic salt of MM 4550A and amoxycillin.

14. A composition according to claim 13 wherein each dosage unit contains from 100 to 1,000 mg of a pharmaceutically acceptable di-basic salt of MM 4550A and amoxycillin.

15. A method of treating bacterial infections in humans and animals which comprises administering to a human or animal in need thereof an antibacterially effective amount of a pharmaceutical composition which comprises a synergistically effective amount of a pharmaceutically acceptable di-basic salt of MM 4550A which is at least 70% pure and an antibacterially effective amount of amoxycillin which substance MM4550A is a solid carboxylic acid of the molecular formula $C_{13}H_{16}O_9N_2S_2$ which in the form of a substantially pure sodium salt has the following characteristics:
    (a) in aqueous solution, it has a characteristic ultraviolet spectrum with absorption maxima at about 238 nm and at about 287 nm;
    (b) when present at 0.4% w/w in a freshly prepared KBr disc, it has a characteristic infra-red spectrum substantially as shown in FIG. 2 and has absorption maxima at inter alia about 3450, 2950, 1765, 1695, 1510, 1390 and 1260 cm$^{-1}$;
    (c) it has a characteristic n.m.r. spectrum which when taken in $D_2O$ is substantially as shown in FIG. 3, which spectrum possesses inter alia (i) a pair of low field doublets centred approximately at 2.45τ and 3.65τ with coupling constants of approximately 15 Hz; (ii) a doublet centred at approximately 8.55τ; and (iii) a sharp singlet at approximately 7.95τ;
    (d) it possesses antibacterial activity against various aureus, *Bacillus subtilis, Escherichia coli, Klebsiella aerogenes, Proteus mirabilis, Acinetobacter anitratus, Serratia marcescens* and *Shigella sonnei;*
    (e) it synergizes the antibacterial activity of ampicillin against certain β-lactamase producing bacteria including strains of *Escherichia coli, Klebsiella aerogenes, Proteus mirabilis, Proteus morganii* and *Staphylococcus aureus Russell;* and
    (f) it is not a polypeptide or protein, in combination with a pharmaceutically acceptable carrier, said di-basic salt of MM 4550A and said amoxycillin being present in the ration of 10:1 to 1:10.

16. A method according to claim 15 wherein the ratio is from 3:1 to 1:3.

17. A method according to claim 15 wherein the pharmaceutically acceptable di-basic salt of MM 4550A is at least 80% pure.

18. A method according to claim 17 wherein the pharmaceutically acceptable di-basic salt of MM 4550A is at least 90% to 100% pure.

19. A method according to claim 15 wherein the pharmaceutically acceptable di-basic salt of MM 4550A is in the form of an alkali metal salt.

20. A method according to claim 15 wherein the pharmaceutically acceptable di-basic salt of MM 4550A is the sodium, potassium, calcium, magnesium, aluminum or ammonium salt.

21. A method according to claim 15 wherein the pharmaceutically acceptable di-basic salt of MM 4550A is in the form of the di-sodium salt.

22. A method according to claim 15 wherein the pharmaceutically acceptable di-basic salt of MM 4550A is in the form of the di-potassium salt.

23. A method according to claim 15 wherein the administration is oral.

24. A method according to claim 15 wherein the administration is parenteral.

25. A method according to claim 15 wherein the administration is by topical application.

26. A method according to claim 15 wherein the composition contains amoxycillin or the acetoxymethyl, pivaloyloxymethyl or phthalidyl ester thereof.

* * * * *